(12) United States Patent
Ma

(10) Patent No.: US 11,779,319 B2
(45) Date of Patent: Oct. 10, 2023

(54) METHOD AND DEVICE FOR LEFT ATRIAL APPENDAGE CLOSURE

(71) Applicant: Marvel Medical Technologies LLC, Laguna Hills, CA (US)

(72) Inventor: Jianlu Ma, Irvine, CA (US)

(73) Assignee: Marvel Medical Technologies LLC, Laguna Hills, CA (US)

(*) Notice: Subject to any disclaimer, the term of this patent is extended or adjusted under 35 U.S.C. 154(b) by 557 days.

(21) Appl. No.: 16/926,670

(22) Filed: Jul. 11, 2020

(65) Prior Publication Data
US 2020/0337685 A1 Oct. 29, 2020

Related U.S. Application Data

(62) Division of application No. 15/192,640, filed on Jun. 24, 2016, now Pat. No. 10,709,432.

(51) Int. Cl.
*A61B 17/00* (2006.01)
*A61B 17/12* (2006.01)
*A61B 17/22* (2006.01)

(52) U.S. Cl.
CPC .... *A61B 17/0057* (2013.01); *A61B 17/12122* (2013.01); *A61B 17/12172* (2013.01); *A61B 17/12177* (2013.01); *A61B 2017/00606* (2013.01); *A61B 2017/22044* (2013.01)

(58) Field of Classification Search
CPC .......... A61B 17/0057; A61B 17/12122; A61B 17/12172; A61B 17/12177; A61B 2017/00606; A61B 2017/22044
See application file for complete search history.

(56) References Cited

U.S. PATENT DOCUMENTS

| | | | |
|---|---|---|---|
| 2009/0062841 A1* | 3/2009 | Amplatz | A61B 17/12159 606/200 |
| 2012/0065667 A1* | 3/2012 | Javois | A61B 17/12172 606/213 |
| 2014/0257357 A1 | 9/2014 | Ren | |

FOREIGN PATENT DOCUMENTS

| | | | |
|---|---|---|---|
| CN | 201930098 U | | 8/2011 |
| CN | 103249374 A | | 8/2013 |
| CN | 203953729 U | * | 11/2014 |
| CN | 204147141 U | | 2/2015 |

OTHER PUBLICATIONS

English Summary of Office Action dated 30-30-2020 for corresponding China Application No. 201680041787.3.
Office Action dated 30-30-2020 for corresponding China Application No. 201680041787.3.

* cited by examiner

*Primary Examiner* — Ashley L Fishback
*Assistant Examiner* — Chima U Igboko
(74) *Attorney, Agent, or Firm* — Raymond Sun

(57) ABSTRACT

A left atrial appendage (LAA) closure device that includes an anchor portion having a first segment and a second segment that are connected in spaced-apart manner by a first connector, a sealing portion, and a second connector that connects the anchor portion and the second segment sealing portion. The first segment is adapted to be positioned outside the LAA and in the pericardial sac after deployment of the closure device, and the second segment is positioned between the first segment and the sealing portion inside the LAA.

7 Claims, 8 Drawing Sheets

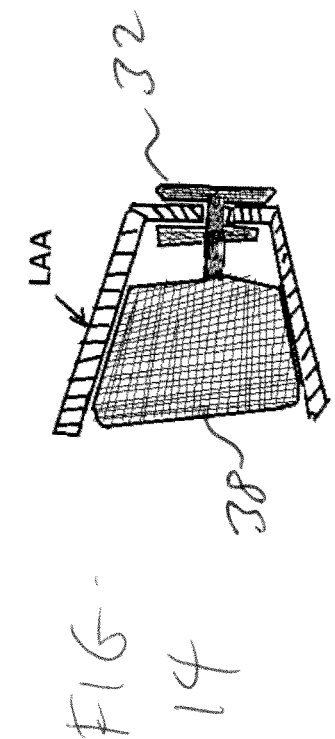
FIG. 12
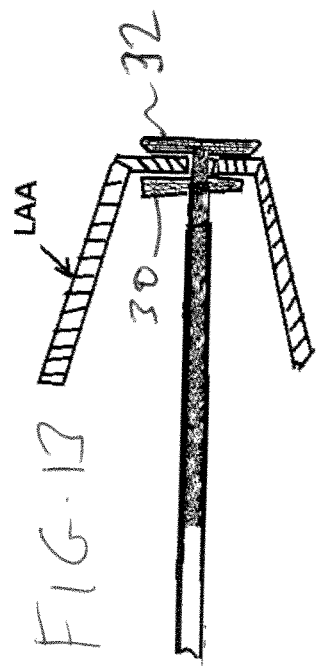
FIG. 14
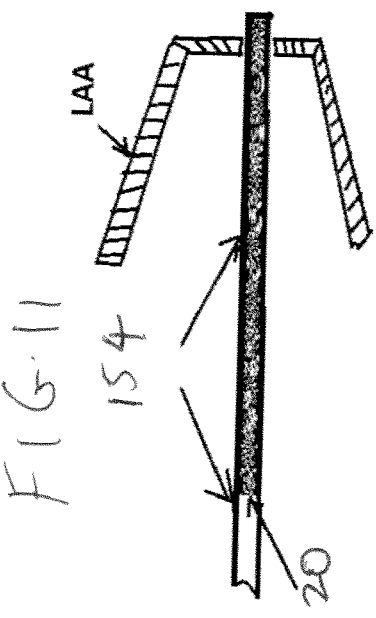
FIG. 11
FIG. 13

METHOD AND DEVICE FOR LEFT ATRIAL APPENDAGE CLOSURE

RELATED CASES

This application is related to Provisional Application No. 62/191,529, filed Jul. 13, 2015, and Provisional Application No. 62/219,609, filed Sep. 16, 2015.

BACKGROUND OF THE INVENTION

Field of the Invention

The present invention relates to a left atrial appendage closure device and methods for delivery and deployment for the closure device.

Description of the Prior Art

FIGS. 1 and 2 illustrate the anatomy of a human heart, including the locations of the left atrial appendage (LAA), the left ventricle LV and the right ventricle RV.

Medical devices for implementing medical procedures for tissue, body lumen and/or cavity closure are known, including those for accessing and closing an appendage. Typically, these devices have employed various tools, which have included tools to access an anatomical area where tissue, lumen or cavity resides, tools to stabilize the tissue, lumen or cavity, tools to deploy a closure device or structure, tools to close the tissue, lumen or cavity with the closure device, and tools to release the closure device. As one particular example, such devices can be used for access and closure of a LAA, either the entire volume or a partial volume, through a percutaneous procedure; i.e., to deliver the device into the LAA sac through the vessels and other vasculature access.

The prior devices and procedures suffer from several drawbacks, First, due to the limited size selection, and mismatch of the device with the LAA geometry, these prior devices tend to migrate out of the LAA post implantation and end up in either the patient's left atrium or left ventricle. Second, existing LAA closure devices do not conform to LAA geometry/profile, and leaves a space or channel around the LAA closure device which allows residual blood flow communication between the left atrium and the LAA, thereby providing more chances for clot formation in the LAA. Third, existing LAA closure devices rely on the spike/barbs on the device itself to anchor the device, which carry with it a greater risk of perforating the left atrium or the LAA, and cause bleeding. Fourth, existing LAA closure devices can distort the LAA and the left atrium.

Thus, there remains a need for a medical device and procedures that facilitate improved access to, and closure of, an appendage in a body vessel.

SUMMARY OF THE DISCLOSURE

In order to accomplish the objects of the present invention, there is provided a left atrial appendage (LAA) closure device that includes an anchor portion having a first segment and a second segment that are connected in spaced-apart manner by a first connector, a sealing portion, and a second connector that connects the anchor portion and the second segment sealing portion. The first segment is adapted to be positioned outside the LAA and in the pericardial sac after deployment of the closure device, and the second segment is positioned between the first segment and the sealing portion inside the LAA.

The present invention also provides a method for deploying a left atrial appendage closure device in an LAA, comprising the steps of:

introducing a guidewire through a femoral or jugular venous puncture and advancing the guidewire through the inferior or superior vena cava into the right atrium of a human heart;

introducing the delivery catheter and dilator over the guidewire to the distal end of the guidewire;

navigating the distal end of the guidewire and the end of the delivery catheter and dilator to the fossa ovalis or atrial septum;

puncturing the fossa ovalis or atrial septum;

advancing the dilator and the delivery catheter through the puncture in the fossa ovalis into the left atrium and advancing until the distal-most portion of the LAA is reached;

advancing a guidewire through the delivery catheter/dilator until a distal end of the guidewire punctures a wall of the LAA, and is located outside the LAA in the pericardial space, alternatively directing pressurized saline solution through the inner lumen of the delivery catheter or dilator at a target location on the wall of the LAA to create the puncture;

remove the delivery catheter and dilator, only leave the guide wire in place.

advancing a delivery sheath that contains a closure device along the guidewire until a distal end of the delivery sheath is positioned at the puncture location of the LAA, with a portion of the distal end of the delivery sheath positioned outside the LAA; and withdrawing the delivery sheath to deploy the closure device in the LAA.

The LAA closure device and method of the present invention provide the following benefits:

1. Design of the Closure Device:
   a. Conformability: the LAA closure device conforms to the natural contour/profile of the LAA and minimizes the potential distortion to the LAA geometry (i.e., the left atrium).
   b. Complete closure of the LAA: the closure device of the present invention conforms to the natural contour/profile of the LAA, and seals the neck/orifice and opening of the LAA completely. There is no residual communication between the left atrium and LAA once the closure device is implanted in the LAA.
   c. No migration: the closure device of the present invention has a built-in anchoring feature and prevents the closure device from potential migration (e.g., away from to LAA and entering the left atrium or left ventricle) after implantation.
   d. Minimizes potential damage to the LAA and/or left atrium wall: the closure device of the present invention does not have anchoring spikes/barbs, or other anchoring features on the LAA closure device, thereby minimizing the risk of perforating the LAA or the left atrium.
   e. LAA volume: the closure device of the present invention has volume, and therefore allows the natural size/volume of the LAA to be maintained after implantation.
2. Method:
   a. One embodiment uses hydraulic pressure/energy to penetrate the LAA wall during the procedure, which is less traumatic and minimizes the potential to perforate the pericardium sac of the heart and other surrounding organs/tissue during the procedure.

b. Makes it possible to close the access channel at the septal wall between the right atrium and the left atrium in the same procedure, without using a separate closure device.

BRIEF DESCRIPTION OF THE DRAWINGS

FIGS. 6-14 illustrate one method for deploying the LAA closure device of FIG. 3 inside a LAA.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

Figure 1:
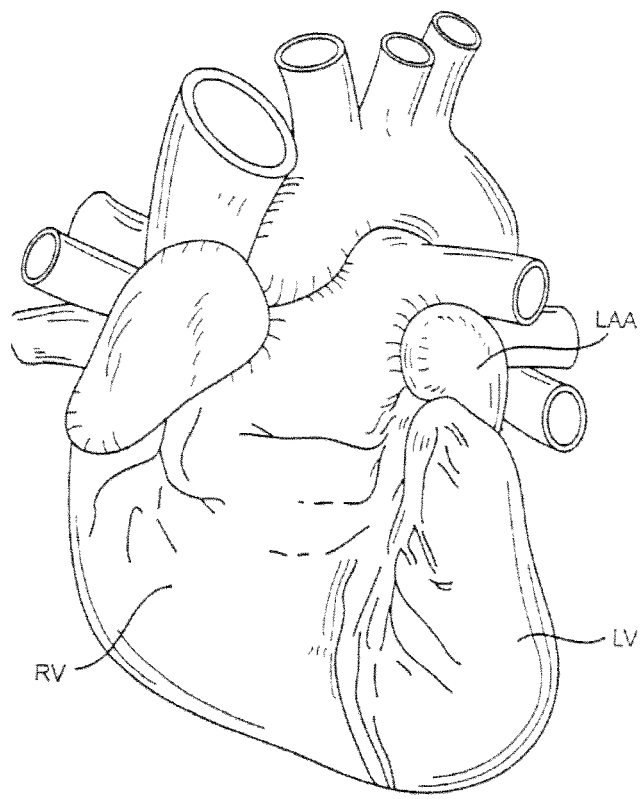
FIG. 1 is schematic view of a human heart.
Figure 2:
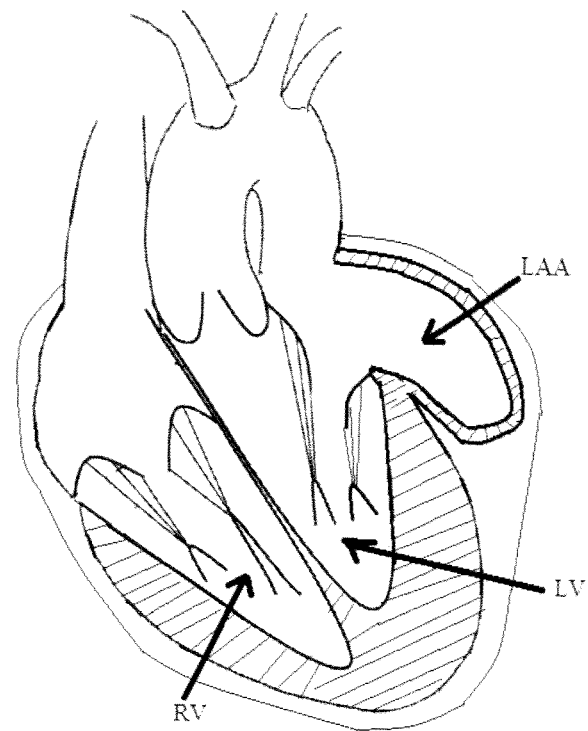
FIG. 2 is a cross-sectional view of a human heart.
Figure 3:
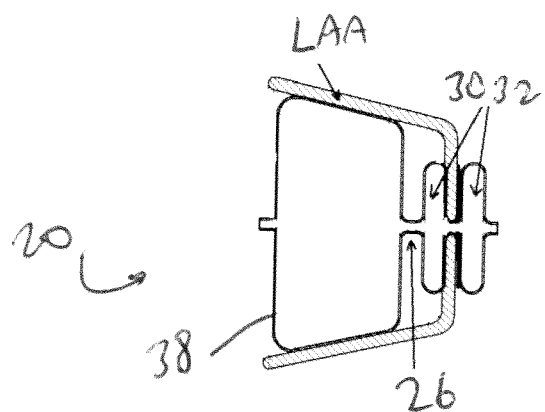
FIG. 3 is a cross-sectional view illustrating a LAA closure device according to one embodiment of the present invention shown implanted inside the LAA.
Figure 4:
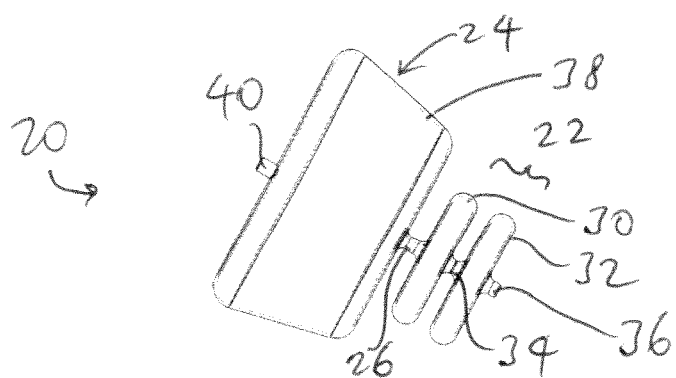
FIG. 4 is a schematic side view of the LAA closure device of FIG. 3.
Figure 5:
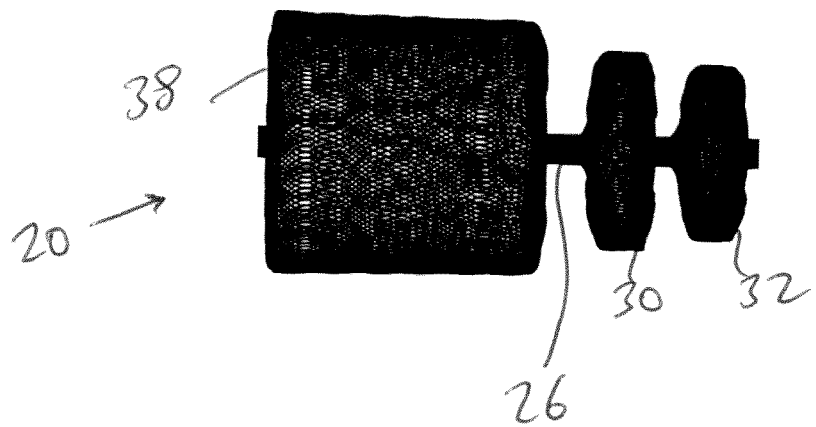
FIG. 5 illustrates the LAA closure device of FIG. 3 as embodied in the form of a braided wire.
Figure 6:
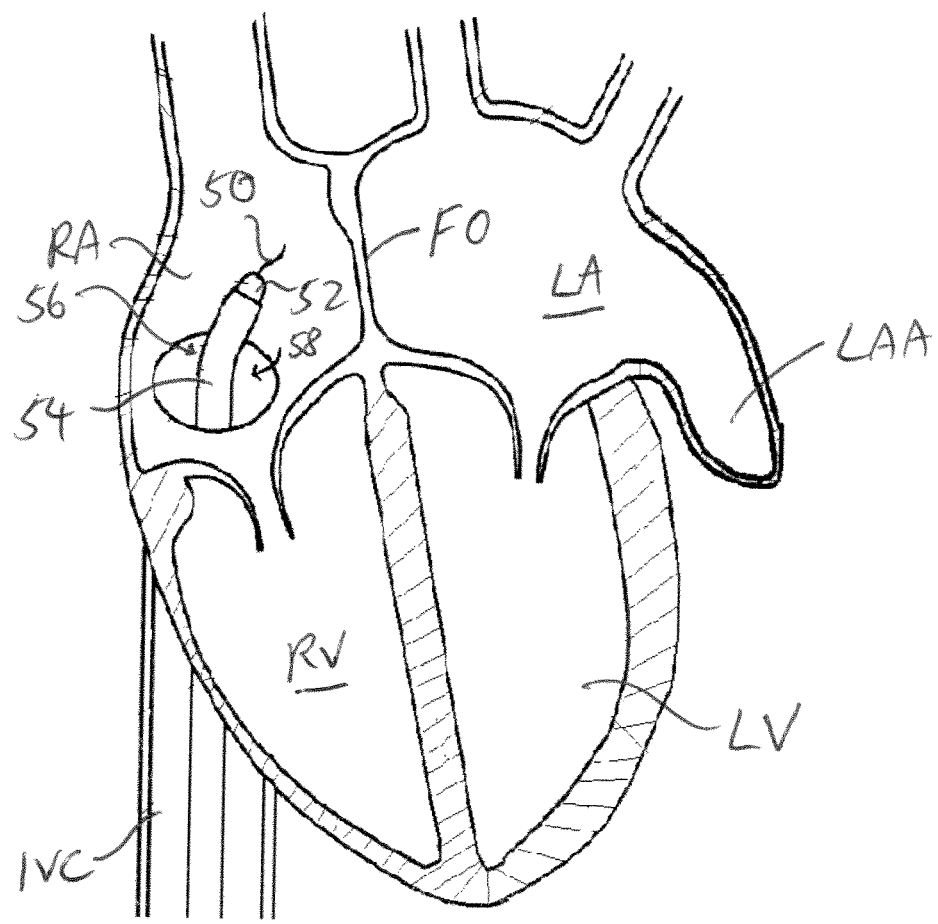

FIGS. 3-5 illustrate one embodiment of an LAA closure device 20 according to the present invention. The LAA closure device 20 has an anchor portion 22, a sealing portion 24 and a connector 26 that connects the anchor portion 22 and the sealing portion 24. The three components can be embodied as one integral piece that is made out of a braided wire, and provided in separate pieces and joined together. The combined LAA closure device 20 has a compacted profile for delivery, and an expanded profile when deployed.

The anchor portion 22 can be positioned either at the tip of the LAA, or at the left atrium position. The anchor portion 22 comprises two disc segments 30 and 32 that are connected by a connector 34. The segment 32 is adapted to be positioned outside the LAA and in the pericardial sac after deployment, and the segment 30 is positioned between the segment 32 and the sealing portion 24. A braided end 36 can be provided outside the segment 32 to function as a collector for the ends of all the wires that are braided. The two segments 30 and 32 are sized and configured to sandwich the LAA wall tissue or the left atrium wall tissue between them, Each segment 30 and 32 can either be circular or non-circular (e.g., oval shape), and have a dimension (such as a diameter) along a long axis LA (see FIG. 4), with the dimension between 5 mm to 100 mm, and a dimension (such as a diameter) along a short axis SA having a dimension between 3 mm to 100 mm, and a height/thickness H between 2 mm to 90 mm. Each segment 30 and 32 can also have a variable cross sectional area. For example, the edges of the segments 30, 32 can have a greater thickness than at their centers, or vice versa. The variable cross sectional area can help the segments 30 and 32 to better conform to the LAA or left atrium wall, thereby providing a better sealing effect. Finally, the distance between the two segments 30 and 32 (i.e., the length of the connector 34) is preferably between 1 mm to 10 mm.

The sealing portion 24 can be embodied in the form of a braided or laser cut container 38 with a generally cylindrical wall structure, and can have a polymer cover material surrounding it. The cylindrical wall structure of the container 38 can have either a circular or non-circular cross-section (e.g., oval shape), and have a dimension in a long axis between 5 mm to 500 mm, and a dimension in a short axis between 3 mm to 300 mm, and a height between 2 mm to 500 mm. The container 38 can also have a variable cross-sectional area, such as shown in FIGS. 3 and 4 where the diameter gradually increases in a tapered manner from the connector 26 towards its outer end, where the ends of the braided wires are collected into another braided end 40, The container 38 is deformable and can be compliant to the internal shape/profile of the LAA.

The connector 26 connects the sealing portion 24 and the segment 30. The connector 26 can have a diameter between 0.5 mm to 90 mm, and length between 0.5 mm to 90 mm.

One example is illustrated in FIG. 3, where the two segments 30 and 32 of the anchor portion 22 sandwich the LAA tissue or left atrium tissue by itself to anchor the LAA closure device 20, with the sealing portion 24 positioned inside the LAA to reduce the volume and/or to exclude the dead space/volume inside the LAA. Here, the sealing portion 24 is at the mouth of the LAA in left atrium, and functions to seal the mouth of the LAA and to occupy the entire or partial volume of the LAA.

The LAA closure device 20 can either be made from a braided structure from biocompatible metallic or polymer materials, or the combination of the two. The LAA closure device 20 can also be made from laser cutting structures from tubing or thin sheet material. The LAA closure device 20 can also contain both braided and laser cutting structures. The LAA closure device 20 can have a polymer cover or coating for improved sealing and healing effect. It can also have surface bio-agents and/or drug coating if preferred.

The present invention provides two methods for delivering the LAA closure device 20. Referring to FIGS. 6-14, the first method uses a guidewire to perforate the LAA wall. First, a guidewire 50 is introduced through a femoral or jugular venous puncture and advanced through the inferior or superior vena cava (IVC) and an opening in the right atrium RA of the heart. See FIG. 6. The introduction of the guidewire 50 into the body may be performed using transesophageal echocardiography and fluoroscopy. A dilator 52 is then advanced over the guidewire 50, and then a sheath 54 of a delivery catheter 56 is advanced over the dilator 52 to adjacent the distal end of the guidewire 50. The catheter 56 can have a pre-bent distal portion 58 on the sheath 54.

Figure 7:
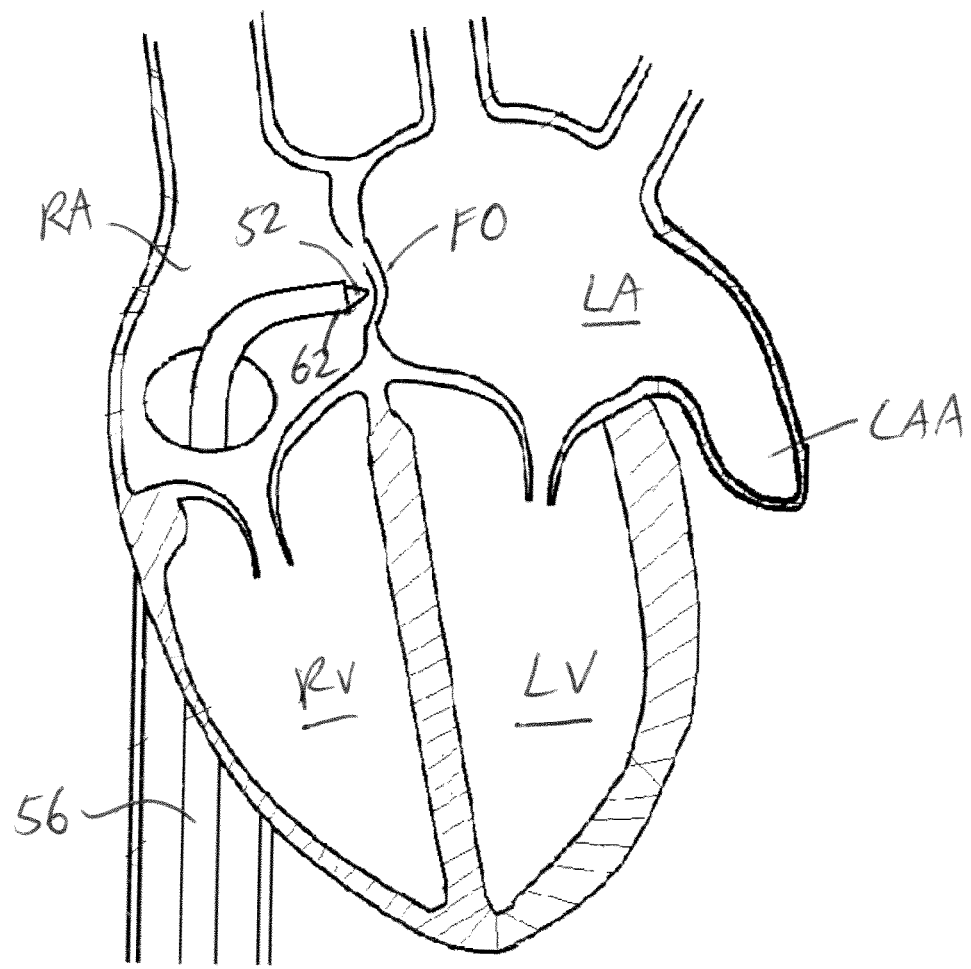

Next, a transspetal puncture is applied at the level of the fossa ovalis FO area to advance the guidewire 50 through the atrial septum of the heart into the left atrium LA of the heart. See FIG. 7. The step of transspetal puncture may be performed using a standard transspetal sheath kit as is known in the art, Specifically, the guidewire 50 is retracted into the dilator 52 and the catheter 56 may be retracted such that the pre-bent distal portion 58 of the sheath 54 facilitates guiding the distal end 62 of the catheter 56 to the fossa ovalis FO as shown in FIG. 7. The positioning of the distal end 62 of the catheter 56 can be confirmed by gently pushing the sheath 54 against the septum between the right atrium and left atrium to "tent" the fossa ovalis FO, with the "tenting" being visible under echocardiography or fluoroscopy or similar visualization techniques.

Figure 8:
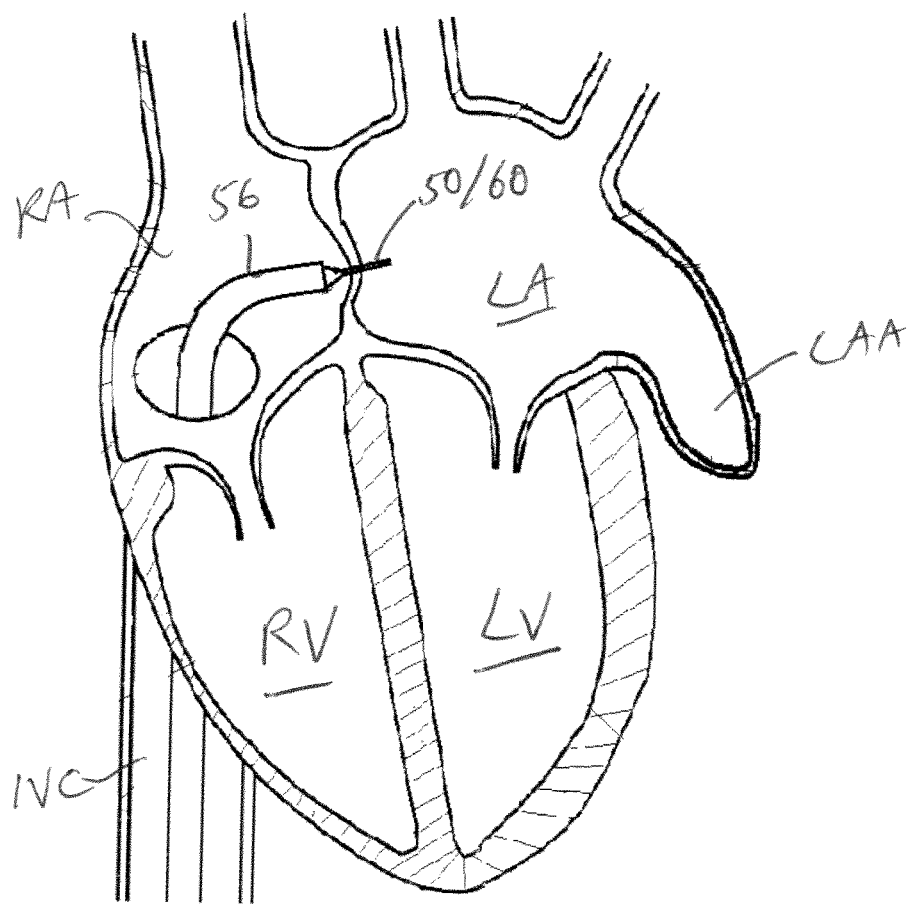
Figure 9:
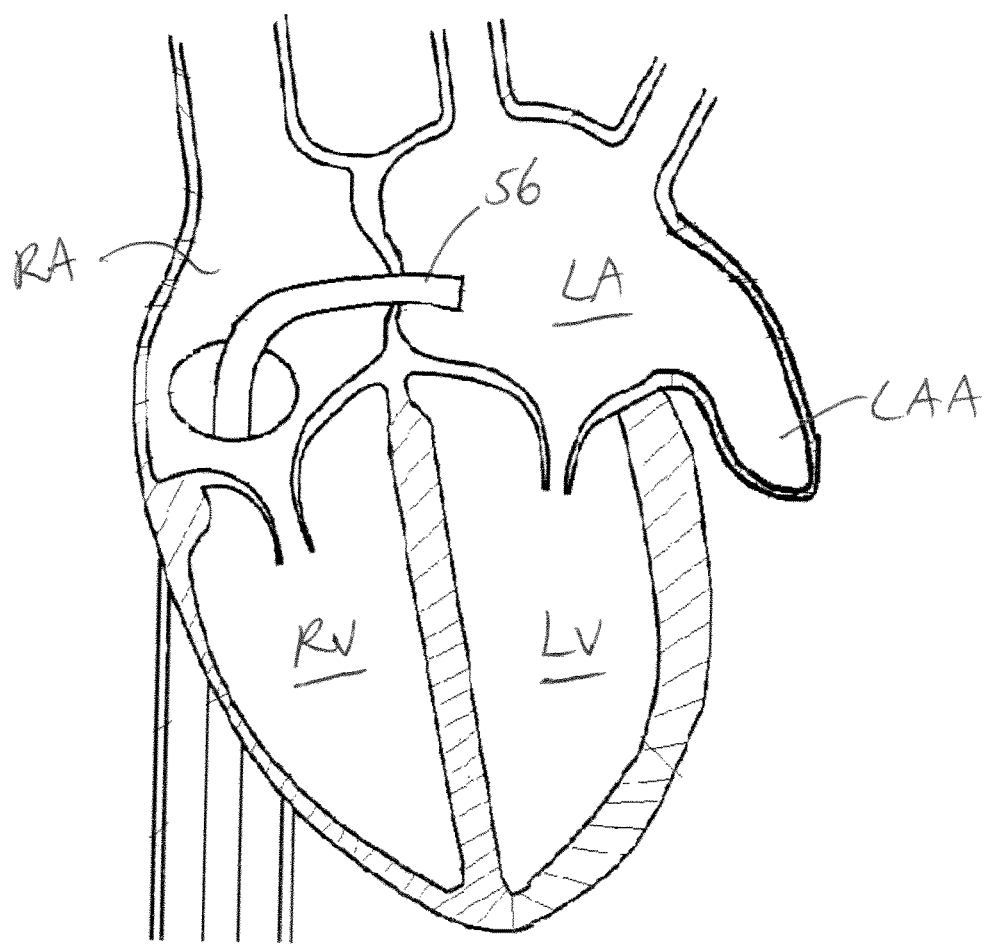
Figure 10:
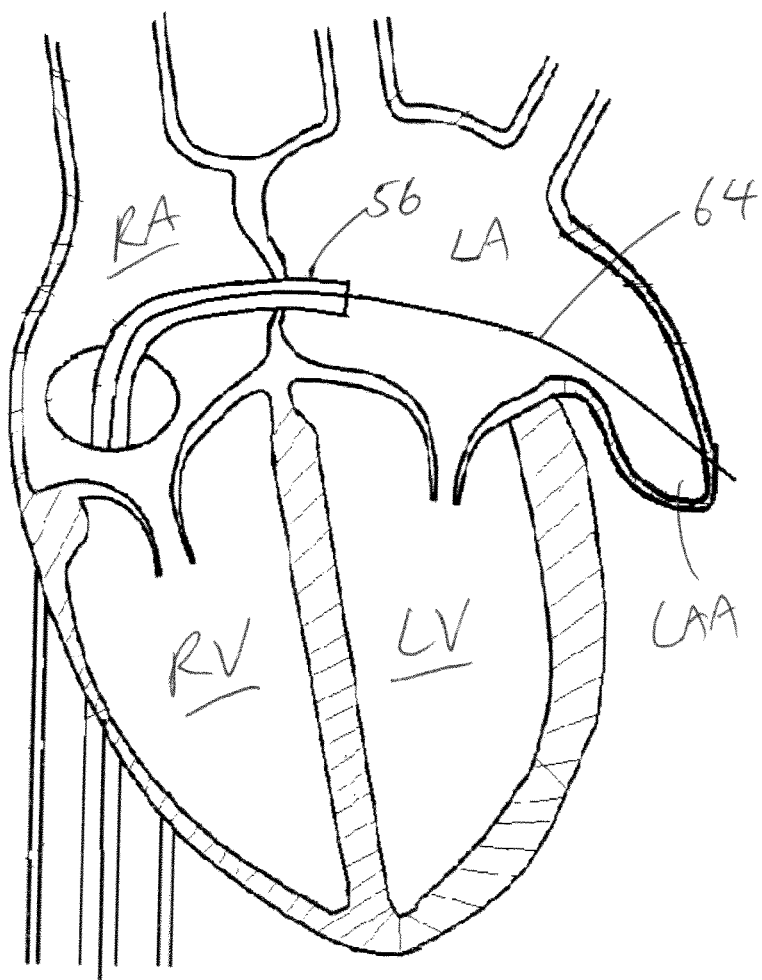

Next, the fossa ovalis FO is punctured, See FIG. 8. The guidewire 50 can be removed from the catheter 56 and then reinserted with its stiffer end entering the catheter 56 first to be used as the puncturing mechanism. Alternatively, after the guidewire 50 has been removed, a transspetal puncture needle 60 can be advanced through the catheter 56 to the distal end 62. Then, either the needle 60 or the stiffer end of the guidewire 50 is advanced out of the distal end 62 of the catheter 56 and used to establish a puncture in the fossa ovalis FO. This step can also be carried out under echocardiography or fluoroscopy or similar visualization techniques. The sheath 54, the dilator 52 and the catheter 56 can all be advanced through the puncture in the fossa ovalis FO into the left atrium LA. The needle 60 or the guidewire 50 can then be removed from the catheter 56, leaving the catheter 56 in the left atrium LA. See FIG. 9.

With the catheter 56 in the left atrium LA, a delivery guidewire 64 (which can be the same as the original guidewire 50) is advanced through the catheter 56 until the distal end 62 of the catheter 56 enters the LAA. The guidewire 64 is further advanced inside the LAA until the distal tip of the guidewire 64 punctures the wall of the LAA and is located outside the LAA in the pericardial space. See FIG. 10. The dilator 52 and the sheath 54 are then removed from the catheter 56, leaving only the guidewire 64 inside the left atrium LA. The guidewire 64 will be used to guide the LAA closure device 20 into the LAA.

Once the perforation in the LAA wall has been created, another delivery sheath 154 (with the LAA closure device loaded in it) is advanced along the guidewire 64, so that the segment 32 of the anchor portion 22 is positioned in the pericardial space outside of the LAA. See FIG. 11. Next, the delivery sheath 154 is withdrawn to allow the segment 32 (or the entire anchor portion 22) to be deployed outside of the LAA. See FIG. 12. Further withdrawal of the delivery sheath 154 will allow the segment 30 of the anchor portion 22 of the LAA closure device 20 to deploy inside the LAA (see FIG. 13) and then the sealing portion 24 to deploy inside the LAA (see FIG. 14). Finally, the delivery sheath 154 and the guide wire 64 are removed, and the puncture site at the femoral vein or jugular vein is closed.

Referring to FIGS. 6-9 and 11-14, the second method uses hydraulic pressure to perforate the LAA wall. The first four steps of this method are the same as the first four steps for the first method, as shown in FIGS. 6-9. At this point, the guidewire 50 is removed from the dilator 52, the distal end 62 of the catheter 56 and the dilator 52 is positioned inside the LAA and positioned at the desired puncture site. Then, pressurized saline solution is injected through the inner lumen of the dilator 52 towards the inner wall of the LAA. The catheter 56 and dilator 52 combination is advanced as the saline injection continues, until the LAA wall is perforated and the distal end of the catheter 56 and dilator 52 combination extends outside of the LAA and is positioned in the pericardial space of the heart (outside of the LAA). See FIG. 11. Next, the guidewire 64 is inserted through the lumen of dilator 52, and advanced until the distal tip of the guidewire 64 is outside of the LAA (in the pericardial space). Then, the dilator 52 and catheter 56 combination is removed, leaving the guidewire 64 in place. Next, the delivery sheath 154 (with the LAA closure device loaded in it) is advanced along the guidewire 64, so that the segment 32 of the anchor portion 22 is positioned in the pericardial space outside of the LAA. See FIG. 11. Next, the delivery sheath 154 is withdrawn to allow the segment 32 (or the entire anchor portion 22) to be deployed outside of the LAA. See FIG. 12. Further withdrawal of the delivery sheath 154 will allow the segment 30 of the anchor portion 22 of the LAA closure device 20 to deploy inside the LAA (see FIG. 13) and then the sealing portion 24 to deploy inside the LAA (see FIG. 14). Finally, the delivery sheath 154 and the guidewire 64 are removed, and the puncture site at the femoral vein or jugular vein is closed.

The above detailed description is for the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, components, mechanisms and methods are omitted so as to not obscure the description of the present invention with unnecessary detail.

What is claimed is:

1. A left atrial appendage (LAA) closure device that is deployed in an LAA, the LAA having a wall and an opening to the left atrium, comprising:
   an anchor portion that has a first segment and a second segment that are connected in spaced-apart manner by a first connector, the first segment and the second segment each having a diameter, the second segment is a single disc member, and wherein the first connector is sized to have a smaller diameter than the first segment and the second segment so that an annular space is defined between the first segment and the second segment;
   a sealing portion that is configured as a container having a cylindrical wall structure that has a diameter that is greater than the diameter of the first segment; and
   a second connector that connects the second segment and the sealing portion;
   wherein when the closure device is deployed inside an LAA, the first connector is positioned in a puncture opening in the LAA wall, the first segment positioned outside the LAA in the pericardial space, and the sealing portion is positioned adjacent the opening to the left atrium; and
   wherein each of the first and second segments is a disc member, and each disc member has a diameter between 3 mm to 100 mm, and a thickness between 2 mm to 90 mm.

2. The device of claim 1, wherein the container has an outer end adjacent the opening to the left atrium, and wherein the container has a variable cross-sectional area where the diameter gradually increases in a tapered manner from the second connector towards the outer end.

3. The device of claim 1, wherein the sealing portion is formed from braided wires, and the ends of the braided wires are collected into a braided end.

4. The device of claim 1, wherein the first segment is a disc member.

5. The device of claim 1 wherein the container has a largest diameter between 3 mm to 300 mm, and a height between 2 mm to 500 mm.

6. A left atrial appendage (LAA) closure device that is deployed in an LAA, the LAA having a wall and an opening to the left atrium, comprising:
   an anchor portion that has a first segment and a second segment that are connected in spaced-apart manner by a first connector, the first segment and the second segment each having a diameter, and wherein the first connector is sized to have a smaller diameter than the first segment and the second segment so that an annular space is defined between the first segment and the second segment;

a sealing portion that is configured as a container having a cylindrical wall structure that has a diameter that is greater than the diameter of the first segment; and a second connector that connects the second segment and the sealing portion;

wherein when the closure device is deployed inside an LAA, the first connector is positioned in a puncture opening in the LAA wall, the first segment positioned outside the LAA in the pericardial space, and the sealing portion is positioned adjacent the opening to the left atrium; and wherein each of the first and second segments is a disc member, and each disc member has a diameter between 3 mm to 100 mm, and a thickness between 2 mm to 90 mm.

7. The device of claim 6, wherein the container has a diameter between 3 mm to 300 mm, and a height between 2 mm to 500 mm.

\* \* \* \* \*